United States Patent [19]

Le Barny et al.

[11] Patent Number: 4,614,608
[45] Date of Patent: Sep. 30, 1986

[54] ORGANIC COMPOUND HAVING A SMECTIC A PHASE, MIXTURE CONTAINING SAID COMPOUND AND PROCESS FOR PRODUCING THE SAME

[75] Inventors: Pierre Le Barny, Orsay; Jean C. Dubois, St. Remy les Chevreuse; Gilles Ravaux, Les Ulis, all of France

[73] Assignee: Thomson-CSF, Paris, France

[21] Appl. No.: 711,366

[22] Filed: Mar. 13, 1985

[30] Foreign Application Priority Data

Mar. 16, 1984 [FR] France .............................. 84 04109

[51] Int. Cl.$^4$ .......................... C09K 3/34; G02F 1/13; C07C 69/76
[52] U.S. Cl. ........................ 252/299.64; 252/299.5; 560/62; 560/65; 560/73; 560/108; 560/98; 350/350 S
[58] Field of Search ............ 252/299.01, 299.6, 299.64, 252/299.67; 560/62, 65, 73, 108; 350/350 S

[56] References Cited

U.S. PATENT DOCUMENTS

| | | | |
|---|---|---|---|
| 4,212,762 | 7/1980 | Dubois et al. | 252/299.64 |
| 4,222,888 | 9/1980 | Dubois et al. | 252/299.64 |
| 4,256,656 | 3/1981 | Beguin et al. | 252/299.6 |
| 4,382,012 | 5/1983 | Eidenschink et al. | 252/299.6 |
| 4,393,231 | 7/1983 | Misaki et al. | 252/299.67 |
| 4,480,117 | 10/1984 | Takatsu et al. | 252/299.64 |
| 4,505,837 | 3/1985 | Romer et al. | 252/299.67 |
| 4,526,704 | 7/1985 | Petrizilka et al. | 252/299.64 |
| 4,545,921 | 10/1985 | Dubois et al. | 252/299.6 |
| 4,550,981 | 11/1985 | Petrzilka et al. | 252/299.64 |
| 4,551,264 | 11/1985 | Eidenschink et al. | 252/299.65 |
| 4,551,280 | 11/1985 | Sasaki et al. | 252/299.64 |

FOREIGN PATENT DOCUMENTS

| | | | |
|---|---|---|---|
| 011002 | 5/1980 | European Pat. Off. | 252/299.64 |
| 44759 | 1/1982 | European Pat. Off. | 252/299.64 |
| 57-179134 | 11/1982 | Japan | 252/299.67 |

OTHER PUBLICATIONS

Le Barny et al., MCLC, 1985, vol. 127, pp. 413–429.
Sirutkaitis et al., ADV. in LC Res. & Appl., 1980, pp. 1023–1028.
Beguin et al., J. de Physique, C3, 1979, pp. 9–14.

*Primary Examiner*—Teddy S. Gron
*Assistant Examiner*—Jack Thomas
*Attorney, Agent, or Firm*—Oblon, Fisher, Spivak, McClelland & Maier

[57] ABSTRACT

The invention relates to a group of organic compounds of the 1-(4-hydroxyphenyl)-2-(4'-trifluoromethyl-phenyl)-ethane ester type having a mesomorphous phase of the smectic A type, to the mixtures obtained from said compounds, as well as to the process for producing the molecules of said group. The compound according to the invention is in accordance with the general chemical formula:

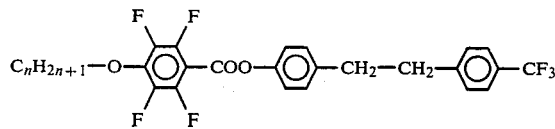

whereby n can be between 1 and 15.

5 Claims, 1 Drawing Figure

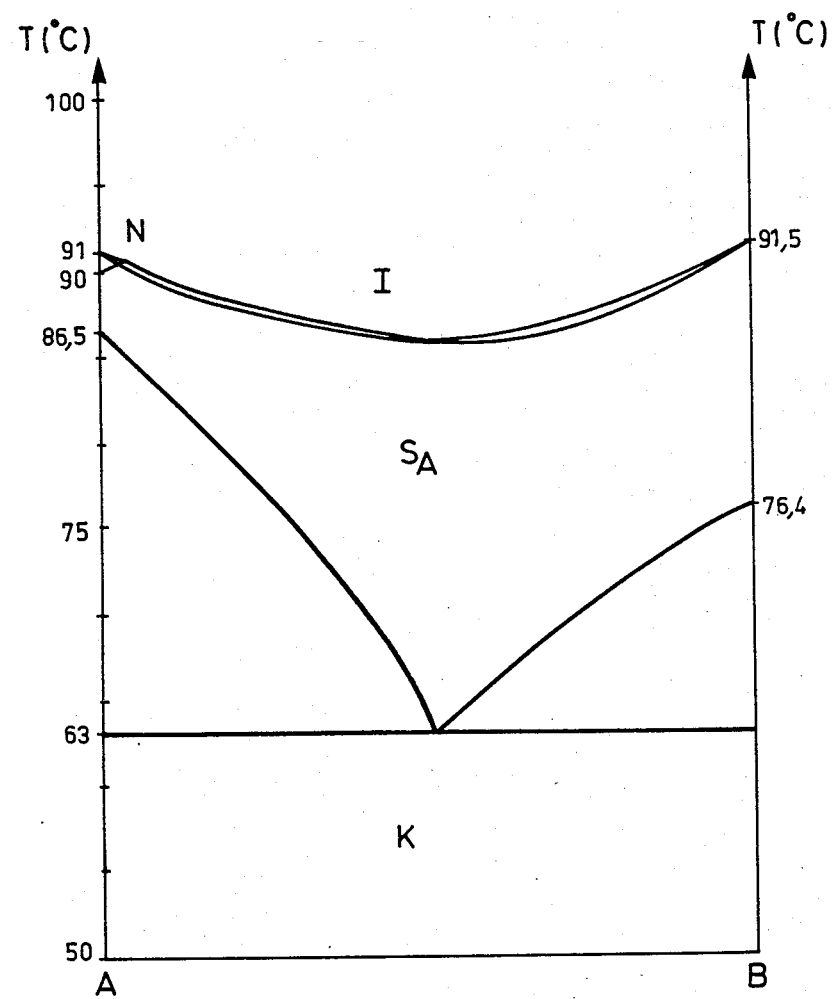

ORGANIC COMPOUND HAVING A SMECTIC A PHASE, MIXTURE CONTAINING SAID COMPOUND AND PROCESS FOR PRODUCING THE SAME

BACKGROUND OF THE INVENTION

The present invention relates to a group of organic compounds of the 1-(4-hydroxyphenyl)-2-(4'-trifluoromethylphenyl)-ethane ester type having a mesophase of the smectic A type and possibly a nematic mesophase. The invention also relates to the process for producing molecules of this group, as well as to the mixtures obtained from these esters and also having a smectic A phase.

The compounds according to the invention have the property, when mixed with smectic A liquid crystals, of widening the smectic range of said products. This is an advantage when such mixtures are used in display means, whose range of use is widened towards both high and low temperatures.

The compounds according to the invention comply with the general chemical formula:

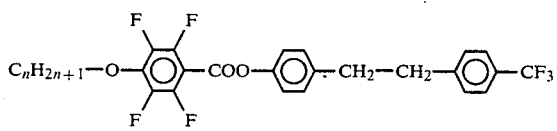

with $1 \leq n \leq 15$.

The compounds in accordance with this formula can be defined by the following name: 1-(4-alkyloxyfluorobenzoyloxyphenyl)-2-(4'-trifluoromethylphenyl)-ethane.

SUMMARY OF THE INVENTION

The invention therefore relates to an organic compound having at least one mesomorphic phase of the smectic A type and which is in accordance with the general chemical formula:

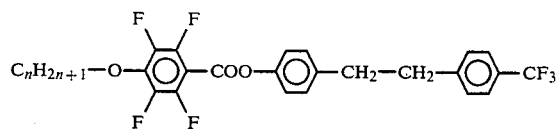

in which $1 \leq n \leq 15$.

The invention also relates to a mixture of liquid crystals having at least one smectic A phase containing at least one of the aforementioned organic compounds.

The invention further relates to a process for the production of an organic compound of the type referred to hereinbefore, wherein said compound is a reaction product of the acid chloride.

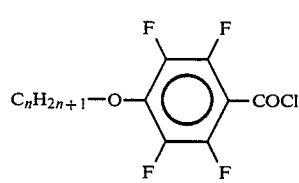

and of the phenol HO

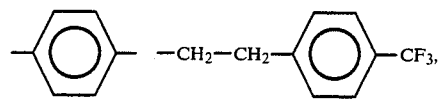

said reaction taking place at ambient temperature in pyridine.

BRIEF DESCRIPTION OF THE DRAWING

The invention will be better understood and further advantages will become more readily apparent from the following description and the attached drawing, which is an isobaric phase diagram.

DESCRIPTION OF THE PREFERRED EMBODIMENTS

The following description relates to the generaly synthesis process of molecules according to the invention, as well as to the mesomorphic properties of the corresponding liquid crystals. Moreover, an example of the incorporation of a compound according to the invention into a smectic A material intended for a display using a mixed thermal and electrical effect will make readily apparent the widening of the range of use of said display towards high and low temperatures.

GENERAL SYNTHESIS PROCESS

The organic compounds according to the invention can be obtained in eight stages from basic products such as 4-bromobenzoic acid, methoxybenzene, pentafluorobenzoic acid and in accordance with the following reaction diagram.

Reaction 1: Obtaining 4-bromophenylacetyl chloride. This acid chloride is obtained by the action of thionyl chloride on 4-bromophenylacetic acid.

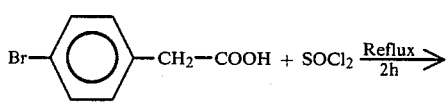

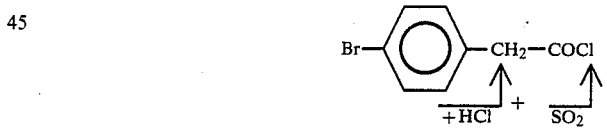

Reaction 2: Synthesis of 4-(4-bromophenylacetyl)-4'-methoxyphenyl.

4-(4-bromophenylacetyl)-4'-methoxyphenyl is obtained by the action of 4-bromophenylacetyl chloride on methoxybenzene in the presence of aluminium chloride and methylene chloride at a temperature of 5° C. (FRIEDEL-CRAFT reaction).

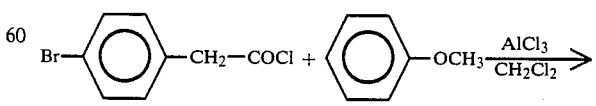

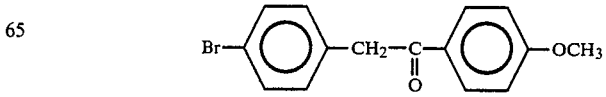

Reaction 3: Obtaining 1-(4-bromophenyl)-2-(4'-methoxyphenyl)-ethane.

4-(4-bromophenylacetyl)-4'-methoxyphenyl is reduced into 1-(4-bromophenyl)-2-(4'-methoxyphenyl)-ethane according to the WOLF-KISHNER reaction, modified by HUANG-MINLON through the action of hydrazine in a basic medium and in the presence of diethylene glycol. The basic medium is obtained by potash.

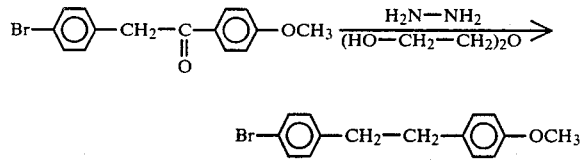

Reaction 4: Synthesis of 1-(4-trifluoromethylphenyl)-2-(4'-methoxyphenyl)-ethane.

1-(4-trifluoromethylphenyl)-2-(4'-methoxyphenyl)-ethane is obtained by trifluoromethylation of 1-(4-bromophenyl)-2-(4'-methoxyphenyl)-ethane in the autoclave at 150° C., using dimethylformamide as the solvent, iodotrifluoromethane as the trifluoromethylation agent and powdered copper as the coupling agent.

ICF₃ +

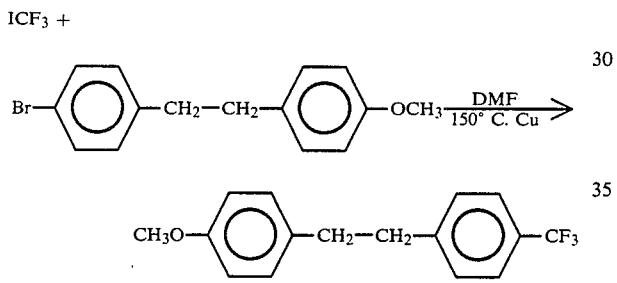

Reaction 5: Synthesis of 1-(4-trifluoromethylphenyl)-2-(4'-hydroxyphenyl)-ethane.

This phenol is obtained by demethylation of 1-(4-trifluoromethylphenyl-2-(4'-methoxyphenyl)-ethane by iodotrimethylsilane at ambient temperature in the presence of chloroform. The reaction time is approximately 5 days.

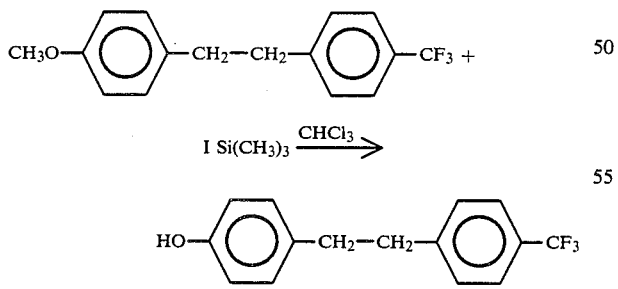

Reaction 6: Synthesis of 4-alkyloxyfluorobenzoic acids.

4-alkoxyfluorobenzoic acids are obtained in one stage from pentafluorobenzoic acid through the action of sodium alkoxide on sodium pentafluorobenzoate, the solvent being the corresponding alcohol, then by acidifying the reaction mixture at the end of the reaction. The reaction takes place at 60° C. and lasts 48 hours.

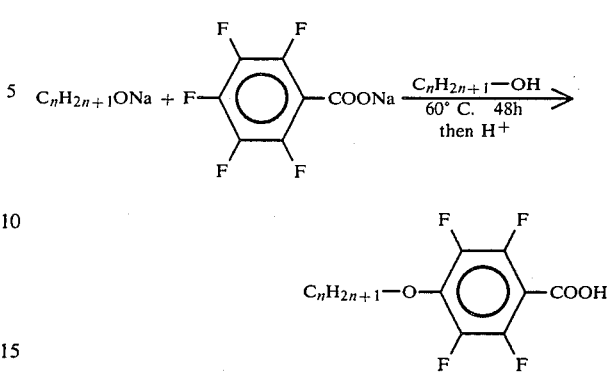

Reaction 7: Synthesis of 4-alkoxyfluorobenzoyl chlorides.

The acid chlorides are obtained by the action of thionyl chloride on 4-alkoxyfluorobenzoic acids.

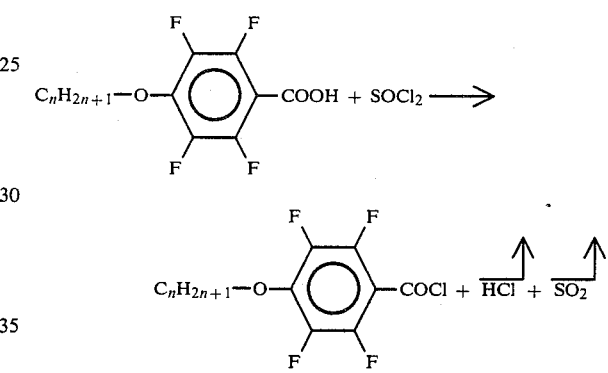

Reaction 8: Synthesis of (4-alkyloxyfluorobenzoyloxyphenyl)-2-(4'-trifluoromethylphenyl)-ethane.

The synthesis of these esters takes place in one stage from the acid chloride,

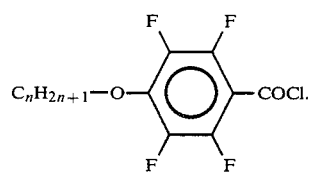

and the phenol

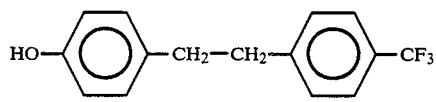

obtained by reaction 5. Reaction 8 takes place at ambient temperature in pyridine.

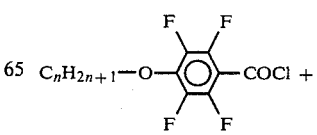

-continued

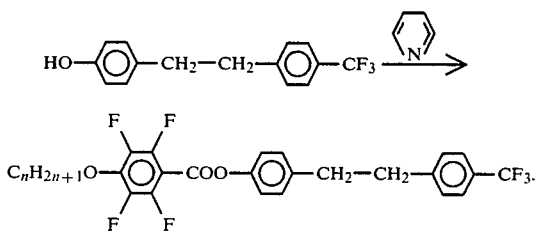

Reactions 1, 2, 3, 7 and 8 are of a conventional nature. Reaction 6 is derived from a known operating mode (cf BURDON, HOLLYHEAD, TATLOW, Journal of the Chemical Society, p. 6336, 1965), but modified according to the teaching of French patent application 82,22074 of the Applicant Company. The aim of this modification is to increase the reaction yield. Reactions 4 and 5 are based on known operating procedures, respectively according to KOBAYASKI, KOMADAKI, SATO, HARA and CHIHAMI (Chemistry and Pharmacy Bulletin No 18, 11, pp. 2334 to 2339, 1970)and JUNG, LYSTER (Journal of Organic Chemistry, No. 42, 23, pp. 3761 to 3764, 1973), these operating procedures being adapted to the preparation of the compounds according to the invention.

OPERATION PROCEDURE OR REACTIONS 4 AND 5

1.: Reaction 4: Trifluoromethylation 70 ml of dimethylformamide (distilled on copper sulphate $CuSO_4$), 12.52 g ($4.43 \times 10^{-2}$ mole) of 1-(4-bromophenyl)-2-(4'-methoxyphenyl)-ethane and 30 g of copper powder are introduced into the 250 ml reactor of the autoclave. The reactor is cooled to $-40°$ C. and 100 h of liquefied iodotrifluoromethane are rapidly introduced. When the reactor has returned to ambient temperature, it is placed in the oven of the autoclave and heated to 150° C. The reaction is allowed to continue at the same temperature for 20 hours, accompanied by stirring.

The cooled reaction medium is poured into 400 ml of water. The copper of the salts are eliminated by filtering on fritted glass No. 4. The insoluble fraction is washed with chloroform. The filtrate is then placed in a separating funnel. The aqueous phase is eliminated. The organic phase is washed with water, then dried on magnesium sulphate $MgSO_4$, filtered and evaporated to dryness in vacuo.

A chestnut coloured oil is obtained, which is washed with water in order to eliminate the residual dimethylformamide. A precipitate appears, which is then dissolved in hexane. The filtrate is evaporated to dryness, which gives 12 g of coloured product.

The crude product is purified by liquid chromatography on silica, with hexane as the eluent, followed by recrystallization in ethanol. Finally, 2.5 g of 1-(4-trifluoromethylphenyl)-2-(4'-methoxyphenyl)-ethane are obtained, whose melting point is 80° C. The reaction yield is 21%.

2: Reaction 5: demethylation 2.51 g (i.e. 8.96 millimole) of 1-(4-trifluoromethylphenyl)-2-(4'-methoxyphenyl)-ethane in 23 ml of distilled chloroform are introduced into a 50 ml Erlenmeyer flask, equipped with a magnetic stirrer. This is followed by the rapid introduction of 2.33 g (i.e. 11.64 millimole) of iodotrimethylsilane. The Erlenmeyer flask is then hermetically plugged and the reaction is allowed to continue for 5 days at ambient temperature. This is followed by the addition of 13 ml of ethanol and stirring is continued for 1 hour, followed by the evaporation in vacuo of the solvents.

The crude product is decolorized by a sodium bisulphite treatment, then purified by liquid chromatography on silica with toluene as the eluent. 1.89 g of phenol are obtained, whose melting point is 126° C. The reaction yield is 79.2%.

The operating procedure described hereinbefore applies no matter what the values of n, provided that the molar proportions are respected.

PROPERTIES OF THE SYNTHESIZED SUBSTANCES

The following table gives in the form of an exemplified embodiment, the results of a calorimetric study performed on two of the compounds according to the invention.

| N | n | K | $S_A$ | N | I |
|---|---|---|---|---|---|
| 1 | 8 | X 86.5 [5.76] | X 90 [0.7] | X 91 [0.5] | X |
| 2 | 11 | X | | 89 [8.9] | X |
| | | | X | (89) [1.2] | X |

In the table, the letters K, $S_A$, N and I respectively designate the crystalline, smectic A, nematic and isotropic phases. THe crosses under these letters indicate the transition from one phase to another, when it takes place. The transition temperatures are given in °C. The values between brackets are heat of transition values in kcal/mole. The value in round brackets is a temperature corresponding to a monotropic phase.

Compound 1, corresponding to n=8, has a smectic A phase of 86.5° to 90° C. and a nematic phase of 90° to 91° C. Compound 2 has a mesophase $S_A$ metastable up to 66.5° C.

The nature of the mesophases has been determined by the study of the isomorphism using the optical microscope of both the investigated compounds and known substances. For example, the attached drawing shows an isobaric phase diagram obtained by contacting compound 1 according to the invention with the substituted 2-hydroxyfluorene ester-type product of formula:

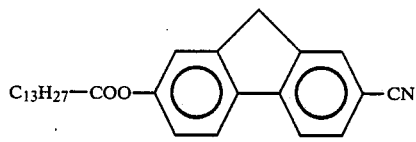

and which has the following succession of phases: K 76.4° C. $S_A$ 91.5° C. I. This ester is described in the aforementioned French Patent application. On this diagram, the left-hand ordinate axis (A) corresponds to 100% of compound 1 according to the invention and the right-hand ordinate axis (B) corresponds to 100% of the aforementioned ester.

It falls within the scope of the present invention to use the present organic compounds as liquid crystals having a smectic A phase alone, mixed with one another or with other liquid smectic A crystals in order to widen the field of application. In this connection, they can be advantageously used in display equipment.

As a non-limitative example, consideration will be given to establishing the influence in a mixture of liquid crystals of the introduction of a compound according to the invention. 4-octyl-4'-cyanobiphenyl (product C) of formula

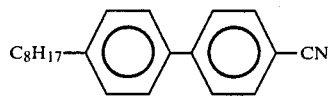

has the phase transition diagram:

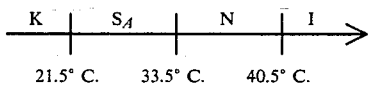

4-decyl-4'-cyanobiphenyl (product D) of formula

has the phase transition diagram

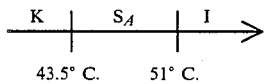

The eutectic formed from products C and D has a melting point of 13° C. and a clarification point of 43.3° C., i.e. a mesomorphic range (compound with a smectic A phase and a nematic phase) extending over 30.3° C. The introduction of 1-(4-octyloxyfluorobenzoyloxyphenyl)-2-(4'-trifluoromethylphenyl)-ethane, i.e. compound 1 in the table, into the aforementioned mixture leads to a ternary eutectic containing 66% of product C, 22.6% of product D and 11.4% of product 1, which has a melting point of 10° C. and a clarification point of 48.6° C. The mesomorphic range (compound with a smectic A phase and a small nematic phase) of the ternary mixture thus extends over 38.6° C. Compared with the binary mixture described hereinbefore, it can be seen that the mesomorphic range is wider and that the temperature limits of the range have been moved upwards and downwards.

What is claimed is:

1. An organic compound having at least one mesomorphic phase of the smectic A type in accordance with the general chemical formula:

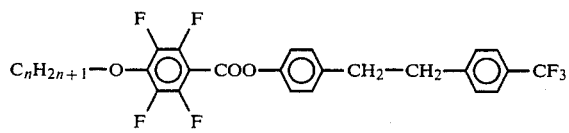

in which $1 \leq n \leq 15$.

2. An organic compound according to claim 1, wherein $n=8$.

3. An organic compound according to claim 1, wherein $n=11$.

4. A mixture of liquid crystals having at least one smectic A phase comprising at least one organic compound according to claim 1.

5. A mixture according to claim 4 containing 66% of 4-octyl-4'-cyanobiphenyl, 22.6% of 4-decyl-4'-cyanobiphenyl and 11.4% of said organic compound for which $n=8$.

* * * * *